(12) United States Patent
Matthis et al.

(10) Patent No.: US 9,034,021 B2
(45) Date of Patent: May 19, 2015

(54) BONE ANCHORING DEVICE

(71) Applicant: Biedermann Technologies GmbH & Co. KG, Donaueschingen (DE)

(72) Inventors: Wilfried Matthis, Weisweil (DE); Lutz Biedermann, VS-Villingen (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/059,196

(22) Filed: Oct. 21, 2013

(65) Prior Publication Data

US 2014/0121712 A1  May 1, 2014

Related U.S. Application Data

(63) Continuation of application No. 13/252,007, filed on Oct. 3, 2011, now Pat. No. 8,591,558, which is a continuation of application No. 12/556,515, filed on Sep. 9, 2009, now abandoned, which is a continuation of application No. 11/482,395, filed on Jul. 7, 2006, now Pat. No. 8,034,089.

(60) Provisional application No. 60/697,670, filed on Jul. 8, 2005.

(30) Foreign Application Priority Data

Jul. 8, 2005 (EP) .................................. 05014840

(51) Int. Cl.
*A61B 17/04* (2006.01)
*A61B 17/86* (2006.01)
(Continued)

(52) U.S. Cl.
CPC ............ *A61B 17/861* (2013.01); *A61B 17/7032* (2013.01); *A61B 17/7037* (2013.01); *A61B 17/7067* (2013.01); *A61B 17/8685* (2013.01); *A61B 17/8875* (2013.01)

(58) Field of Classification Search
USPC .................................. 606/301, 305–309, 318
See application file for complete search history.

(56) References Cited

U.S. PATENT DOCUMENTS 5,501,684 A * 3/1996 Schlapfer et al. ............. 606/301
5,899,904 A   5/1999 Errico et al.
(Continued)

FOREIGN PATENT DOCUMENTS

| | | |
|---|---|---|
| EP | 1 579 816 A1 | 9/2005 |
| KR | 10-0910205 | 7/2009 |
| WO | WO 94/00066 | 1/1994 |

OTHER PUBLICATIONS

European Search Report for Application No. EP 05 01 4840 dated 2 Dec. 2005 (6 pgs.).

*Primary Examiner* — Sameh Boles
(74) *Attorney, Agent, or Firm* — Christie, Parker & Hale, LLP

(57) ABSTRACT

A bone anchoring device has an anchoring element, a receiving portion, and a pressure element. The anchoring element includes a shank to be anchored in a bone or a vertebra and a head, the head having an exterior surface with a spherical segment-shaped portion. The shank and the head are separate parts. The receiving portion includes a first end, a second end opposite to the first end, a longitudinal axis passing through the two ends, a bore coaxial with the longitudinal axis, and a first region adjacent to the second end for receiving a spherical segment-shaped section of the head. The pressure element exerts pressure on the head to lock the head in the receiving portion. The head has a hollow inner portion to receive a free end portion of the shank and wherein the head and the end portion are formed such that the end portion can be elastically clamped by the head.

5 Claims, 5 Drawing Sheets

(51) Int. Cl.
   *A61F 2/08*   (2006.01)
   *A61B 17/88*  (2006.01)
   *A61B 17/70*  (2006.01)

(56) References Cited

U.S. PATENT DOCUMENTS

| | | |
|---|---|---|
| 6,063,090 A | 5/2000 | Schläpfer |
| 6,074,391 A | 6/2000 | Metz-Stavenhagen et al. |
| 6,270,529 B1 * | 8/2001 | Terrill-Grisoni et al. .. 623/20.11 |
| 6,835,196 B2 * | 12/2004 | Biedermann et al. ......... 606/308 |
| 2003/0125741 A1 | 7/2003 | Biedermann et al. |
| 2005/0033298 A1 | 2/2005 | Hawkes et al. |
| 2005/0049588 A1 | 3/2005 | Jackson |
| 2005/0055026 A1 | 3/2005 | Biedermann et al. |
| 2005/0203516 A1 | 9/2005 | Biedermann et al. |
| 2005/0216003 A1 | 9/2005 | Biedermann et al. |
| 2006/0036252 A1 | 2/2006 | Baynham et al. |
| 2006/0217806 A1 | 9/2006 | Peterman et al. |

\* cited by examiner

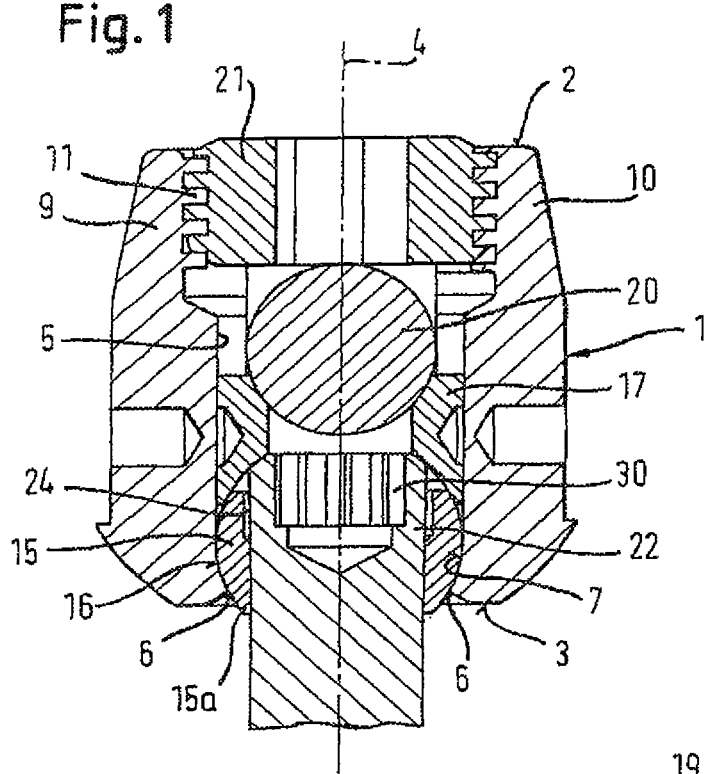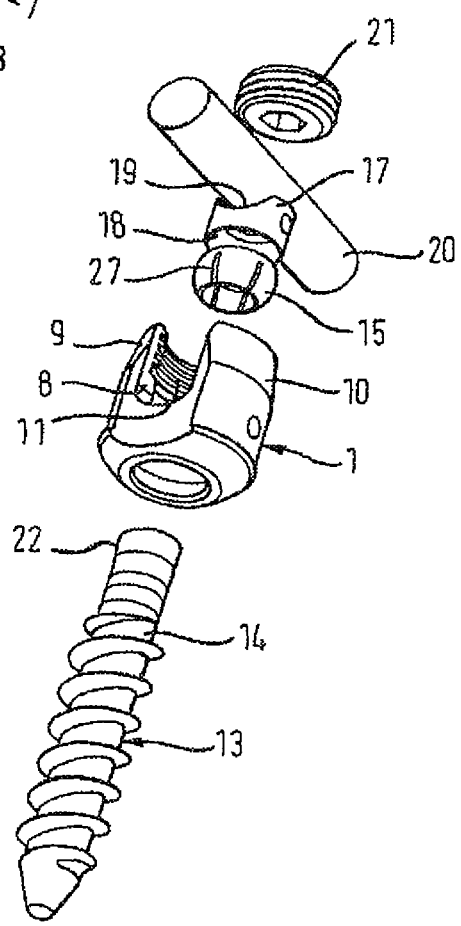

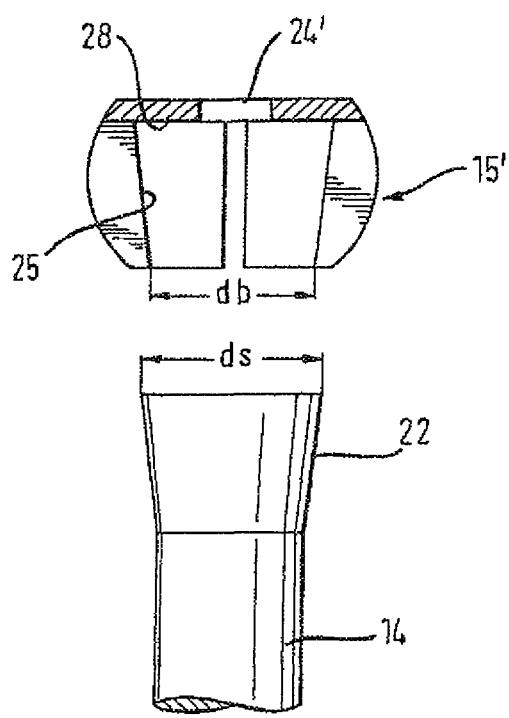
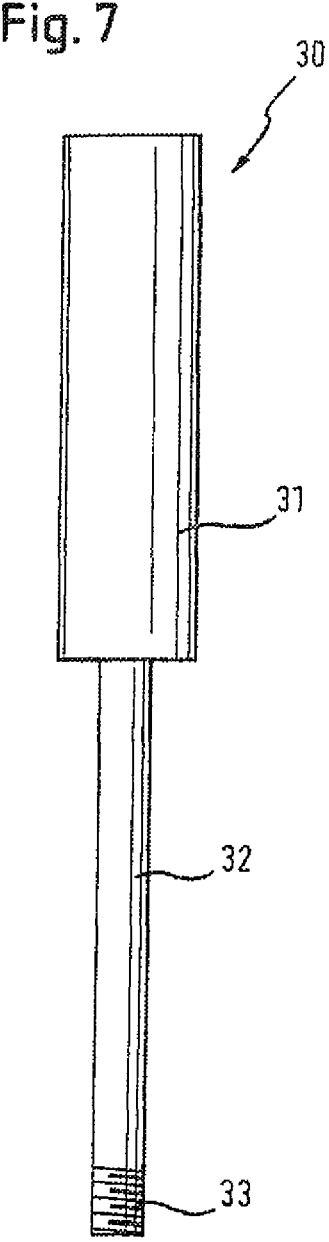

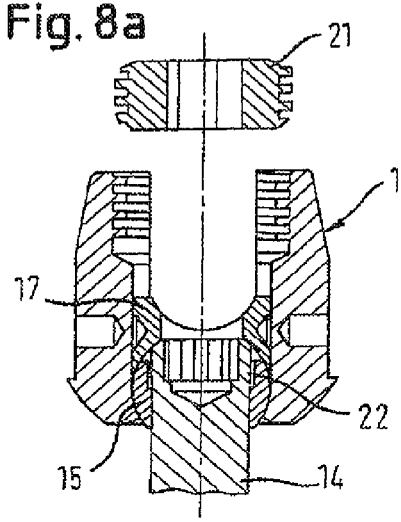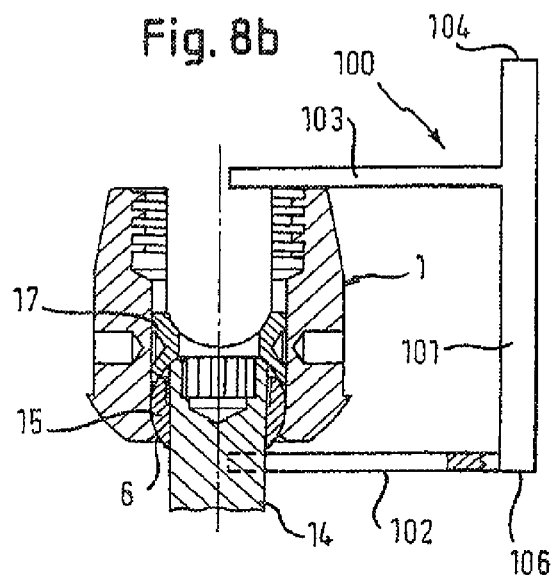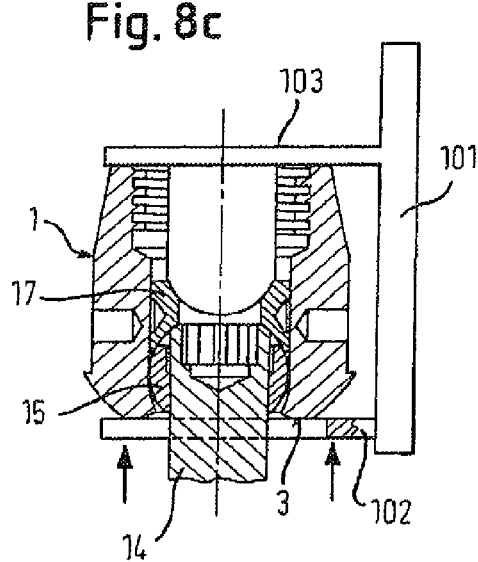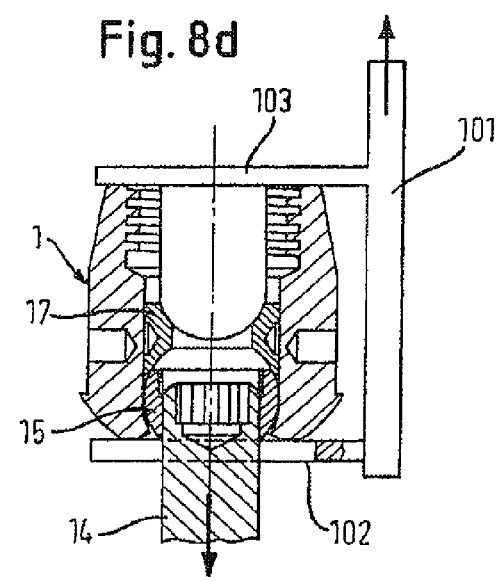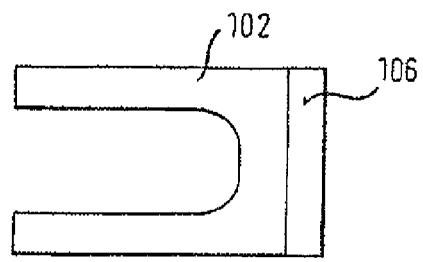

BONE ANCHORING DEVICE

CROSS-REFERENCE TO RELATED APPLICATIONS

This application is a continuation of U.S. application Ser. No. 13/252,007, filed Oct. 3, 2011, which is a continuation of U.S. application Ser. No. 12/556,515 filed Sep. 9, 2009, which is a continuation of U.S. application Ser. No. 11/482,395 filed Jul. 7, 2006, which claims the benefit of U.S. Provisional Application No. 60/697,670, filed Jul. 8, 2005, and claims priority from European Patent Application No. EP 05 014 840.2 filed Jul. 8, 2005, the disclosures of which are incorporated by reference herein.

BACKGROUND

The present disclosure relates to a bone anchoring device comprising an anchoring element which has a shank to be anchored in a bone and a head having an exterior surface with a spherical segment-shaped portion, a receiving portion to receive said head and an element which exerts pressure on said head, wherein said shank and said head are separate parts.

A bone anchoring device of this type is known from U.S. Pat. No. 6,835,196 B2. The shank of the anchoring element has a cylindrical end portion which is received in a corresponding bore in the head which has a spring-yielding edge to clamp said end portion of the shank when pressure is exerted on the head. In another embodiment the end portion of the shank has an outer thread which cooperates with an inner thread of the bore in the head receiving said end portion. With this bone anchoring device it is possible to first screw in the shank, adjusting the length of the shank, if necessary, and then connecting it with the receiving portion containing the head.

U.S. Pat. No. 6,074,391 discloses a bone anchoring device comprising a bone screw having a threaded shank with a spherical section forming a free end of the shank. The bone anchoring device further comprises a receiving part having on the inner side a conically shaped annular surface converging downwardly. A slotted cage provided in the receiving part encompasses the spherical section and has an outer conically shaped surface which cooperates with the conical surface of the receiver part. The slots in the cage allow for the spherical section of the shank being clamped when pressure is exerted onto said cage.

WO 94/00066 discloses an osteosynthetic fixation device consisting of a securing component having a conical head section and an adjoining anchoring component designed for fixing in the bone and a spherical segment-shaped slotted clamping component with a conical bore to receive the conical head section to clamp inside a connecting component having a spherical segment-shaped bore. The clamping component has an outer surface with a spherical segment-shaped portion. The fixation of the securing component inside the connecting component is achieved by pulling the conical head section into the clamping component such that the clamping component is spread to press against the spherical segment-shaped bore of the connecting component.

U.S. Pat. No. 6,063,090 discloses a device for the connection of a rod with a pedicle screw which allows to first screw a screw element with a spherical head into the bone and thereafter to click a retainer head to be connected with the rod onto the spherical head. To fix the angular position of the screw element relative to the retainer head the spherical head is clamped by a conical spring chuck.

SUMMARY

A bone anchoring device according to one or more embodiments of the present disclosure includes a head and a shank as separate parts which facilitates pre-assembling of the device and which additionally provides an enhanced fixation when final tightening of the screw to the rod occurs.

The bone anchoring element according to one or more embodiments of the present invention has the advantage that it allows to combine shanks of different size with the separate head and receiving portion according to the needs in a specific situation during or before surgery.

With the bone anchoring element according to one or more embodiments of the present invention it is possible to first anchor the shank into the bone and thereafter to mount the receiving portion including the spherical segment-shaped head onto the shank. Due to the conical shape of the end portion of the shank and the cooperating recess of the head a pre-fixation of the head relative to the shank is achieved even if the head is not yet locked in its final polyaxial position.

If the cone angle of the end portion of the shank and the recess of the head is in a certain range of about 2 degrees to 10 degrees it is possible to achieve a self-locking connection between the spherical segment-shaped head and the shank which ensures that the head cannot fall off or cannot be separated from the shank unintentionally.

The bone anchoring device further has the advantage that in one or more embodiments of the present invention it is compact as an outer ring or nut is not required.

BRIEF DESCRIPTION OF THE DRAWINGS

Further features and advantages of the invention will become apparent from the description of embodiment in conjunction with the accompanying figures.

FIG. 1 shows a cross-sectional view of the bone anchoring device according to one embodiment of the invention.

FIG. 2 shows an exploded view of the bone anchoring device according to FIG. 1.

FIG. 6 shows a schematic sectional view of a modification of the head connected to the shank.

FIG. 7 shows a schematic side view of a tool to be used with the head of FIG. 6.

FIGS. 8*a* to 8*d* show schematically steps of in situ removal of the head and receiving portion according to FIGS. 1 to 4 together with a tool.

FIG. 9 shows a bottom view of the tool used for the steps according to FIGS. 8*a* to 8*d*.

DETAILED DESCRIPTION

Figure 3:
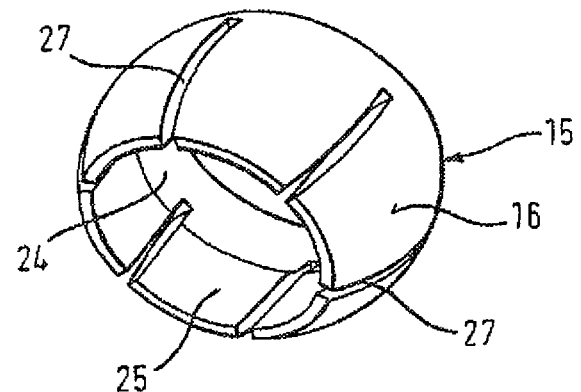
FIG. 3 shows a perspective view of the head of the bone anchoring element which is part of the bone anchoring device according to FIG. 1.

As shown in FIGS. 1 to 3, the bone anchoring device comprises a receiving portion 1 which is substantially cylindrical and has a first end 2 and a second end 3 opposite to the first end. The two ends are perpendicular to a longitudinal axis 4. Coaxially with the longitudinal axis 4, a coaxial bore 5 is provided which extends from the first end 2 to a predetermined distance from the second end 3. At the second end 3 an opening 6 is provided the diameter of which is smaller than the diameter of the bore 5. The coaxial bore 5 tapers towards the opening 6. In the embodiment shown it tapers in the form of a spherically shaped section 7.

The receiving portion 1 further has an U-shaped recess 8 which starts from the first end 2 and extends in the direction of the second end 3 to a predetermined distance from said second end 3. By means of the U-shaped recess two free legs 9, 10 are formed ending towards the first end 2. Adjacent to the first end 2 the receiving portion 1 comprises an internal thread 11 at said legs 9, 10.

The bone anchoring element 13 comprises a shank 14 with a bone thread and a head 15 which is formed as a separate part and which is connected to the shank in the assembled state shown in FIG. 1. The head 15 has a spherical segment-shaped outer surface portion 16. The radius of this portion of the head 15 is such that when the head 15 is received in the receiving portion 1, the spherical outer surface 16 of the head 15 is supported by the spherical section 7 adjacent to the opening 6 at the second end 3 or is supported by the edge of the opening 6 such that a portion 15a of the head 15 projects from the opening 6. If pressure is not yet exerted on the head 15, the head 15 is pivotably held in the spherical region 7 similar to a ball and socket joint.

A pressure element 17 is provided which has a cylindrical construction with an outer diameter which is only slightly smaller than the inner diameter of the bore 5 to allow the pressure element to be introduced into the bore 5 of the receiving portion 1 and to be moved in the axial direction. On its lower side facing towards the second end 3, the pressure element 17 comprises a spherical recess 18, the radius of which corresponds to the radius of the spherical portion 16 of the head 15. On the opposite side the pressure element 17 has a U-shaped recess 19 which extends transversely to the longitudinal axis 4. The lateral diameter of this U-shaped recess is selected such that a rod 20 which is to be received in the receiving portion can be inserted in the recess 19 and guided laterally therein. The depth of the spherical recess 19 is selected such that in an assembled state when the rod is inserted and pressed against the bottom of the U-shaped recess, the pressure element 17 exerts a pressure on the head 15.

The bone anchoring device further comprises an inner screw 21 which can be screwed in between the legs 9, 10 to fix the rod 20 and to exert a pressure via the pressure element 17 on the head 15. The internal thread 11 and the cooperation thread of the inner screw 21 can have any known thread shape. A flat thread or a negative angle thread, however, brings about the advantage that a splaying of the legs 9, 10 does not occur which makes it unnecessary to use an outer nut or ring to prevent the splaying of the legs 9, 10.

Details of the shank 14 and the head 15 will now be described. The shank 14 comprises an end portion 22 to be received in the head 15. The end portion 22 has the shape of a truncated cone widening towards the free end 23 which has a diameter ds. The cone angle α of the conical end portion 22 of the shank is preferably selected such that a self-locking connection can be achieved when the shank is connected to the head. As can be seen in particular in FIGS. 2 and 3, the head 15 has the contour of a flattened sphere and comprises at its end facing towards the first end 2 a bore 24 which is coaxial with the longitudinal axis 4 of the receiving portion and has a diameter slightly larger than the largest diameter ds of the free end 23 of the conical end portion 22. The bore 24 allows for guiding through the free end 23 of the conical end portion 22 such that the conical end portion 22 projects from the head 15 when it is fully inserted, as shown in FIG. 1. On its side directed towards the second end 3 of the receiving portion, the head 15 has a recess 25 shaped as a hollow truncated cone, the dimensions of which are such as to mate with the dimensions of the conical end portion 22 of the shank when the shank is inserted into the head 15. The angle α' of the conical recess 25 preferably corresponds to the angle α of the end portion 22 or is larger than the angle α. The lower opening 26 formed by the recess 25 has a diameter db which is smaller than the largest diameter ds of the free end 23 of the conical end portion 22 of the shank.

As shown in FIGS. 2 and 3, the head 15 has a plurality of longitudinal slits 27 which extend from an outer surface of the head 15 to the recess 25. The slits 27 extend to the end facing the end portion 22 of the shank and are arranged equidistantly in a circumferential direction. The slits 27, are of sufficient size to allow a spreading of the recess 25 to an extent that the lower opening 26 widens to allow insertion of the conical end portion 22 and to elastically clamp the end portion after insertion 22.

Figure 4:
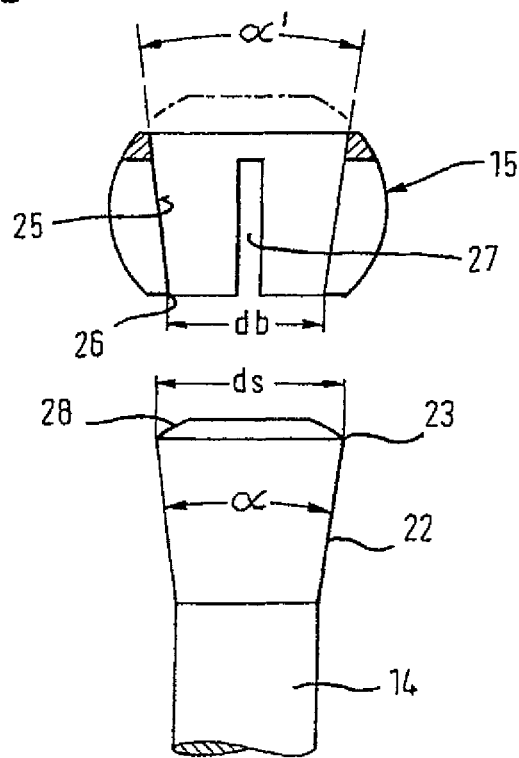
FIG. 4 shows a schematic sectional view of the head and the end portion of the shank of the bone anchoring element of FIGS. 1 to 3.

As shown in FIG. 4, the free end 23 of the conical end portion 22 can have a chamfer 28 for facilitating the insertion into the head 15. The chamfer 28 can be curved so as to mate with the curvature of the recess 18 of the pressure element 17 (see FIG. 2). The conically shaped recess 25 can also extend throughout the head 15.

Preferably, the cone angle α' of the recess 25 of the head 15 corresponds to the cone angle α of the end portion 22 and is selected to achieve a self-locking connection when the conical end portion 22 is inserted into the recess 25 of the head. Once a self-locking connection is established, an additional force is required to remove the conical end portion out of the recess 25 which is greater than the force necessary to insert the conical end portion into the recess 25. The cone angle to achieve a self-locking effect is preferably between approximately 2 degrees to 10 degrees, more preferably about 4 degrees.

In a first mode of operation, a suitable shank 14 is selected and connected with its end portion 22 to the head 15. The introduction of the conical end portion 22 into the head 15 through the lower opening 26 is facilitated by the chamfer 28. By inserting the end portion 22, the lower opening 26 is widened and the conical recess 25 is spread due to the slits 27 so as to allow for the introduction of the whole conical end portion 22. If the angle α is selected such that a self-locking connection is established when the shank is introduced into the head, the head cannot fall off or be removed unintentionally once the shank is inserted into the head.

With reference to FIGS. 1 and 2, the bone anchoring element 13 consisting of the shank 14 with the mounted head 15 is introduced into the receiving portion 1 from the first end 2 with the threaded shank 14 being guided through the opening 6 of the receiving portion until the head 15 rests against the edge of the opening 6. Thereafter, the pressure element 17 is introduced and the threaded shank screwed into the bone. Then, the angular position of the receiving portion 1 relative to the anchoring element 13 is adjusted and the rod 20 is inserted. The rod is then fixed by screwing in the inner screw 21. The inner screw 21 exerts a pressure onto the rod 20 which presses down the pressure element 17. The pressure element 17 forms an abutment for the free end 23 of the end portion 22 of the shank (see FIG. 4). In this manner, the head 15 is pressed against the spherical region 7 or the edge of the opening 6. Consequently, the edge of the opening 6 compresses the head 15, which narrows the recess 25 due to the slits 27, and which causes the head 15 to clamp the end portion 22 of the shank. In addition, the pressure element 17 presses onto the free end 23 of the end portion 22 and thus presses the conically shaped end portion 22 into the conical recess 25 of the head whereby a firm connection between the head and the shank is achieved and simultaneously the head is locked in its rotational position.

The parts of the bone anchoring device described above are preferably made of a body-compatible material, such as, for example, titanium.

In a second mode of operation, first the threaded shank 14 is screwed into the bone or into a vertebra. For this purpose the shank 14 has at its free end known engagement possibilities for a screwdriver, such as a hexagon-shaped recess 30, as shown in FIG. 1. Then the receiving portion 1 together with the loosely preassembled head 15 and pressure element 17 is pressed onto the conical end portion 22 of the shank 14 projecting out of the bone. To accomplish this a certain pressure force is necessary to click the head 15 onto the conical end portion, i.e. the head 15 is spread due to the slits 27 and snaps onto the conical end portion 22. The pressing force required to place the head onto the shank depends on the cone angle and/or the elasticity provided by the slits. In this state the head is still pivotable in the receiving portion while the shank is clamped by the head. Next, the rod 20 is inserted and the angular position of the receiving portion 1 relative to the head 15 is adjusted. Thereafter, the inner screw 21 is screwed in between the legs 9, 10 until it presses on the rod 20, which thereby exerts pressure on the head 15.

Due to the pressure exerted by the pressure element on the head 15, the slotted head 15 is firmly connected or clamped to the shank 14, preventing movement and, at the same time, the head 15 is locked in its rotational position.

If necessary, the receiving portion 1 together with the head 15 can be separated from the shank in situ with a tool as shown in FIGS. 8a to 8d and 9. First, the inner screw 21 and the rod 20 are removed as shown in FIG. 8a. In this state, the head 15 is unlocked in the receiving portion 1 but it still clamps the end portion 22 of the shank. Next, as shown in FIG. 8b, a tool 100 is used to push the head 15 into the receiving portion 1 so that it no longer projects from the lower opening 6 of the receiving portion.

The tool 100 comprises a longitudinal bar 101 from which two arms 102, 103 extend in a perpendicular direction. One of the arms is fixed at a certain distance from a free end 104 of the bar 101 such that a section 105 of the bar projects above the arm 103 to facilitate gripping. In the embodiment shown it is the upper arm 103 when the tool is in use. The other arm 102 is slidingly mounted on the longitudinal bar 101 and can be variably fixed between an end position at the other end 106 and a desired position in a direction towards the upper arm 103 so as to vary the distance between the arms. At least the lower arm 102 is fork shaped so as to be able to encompass the shank 14. The distance between the arms when the lower arm 102 is located at the end 106 of the bar is greater than the height of the receiving portion 1.

In use, the tool is applied to the receiving portion with the lower arm 102 at its end position as shown in FIG. 8b. Then, the lower arm 102 is shifted and pressed against the second end 3 of the receiving portion 1, thus shifting the receiving portion 1 relative to the head 15 until the head 15 is completely within the receiving portion, as shown in FIG. 8c. In this state the head has space to widen so that the end portion 22 of the shank can be pulled out when pulling the tool together with the receiving portion and the head away from the shank as shown in FIG. 8d.

Modifications are possible. For example, the upper arm 103 can be slidable instead of the lower arm. The slidable arm need not be fixed at the bar but can be pressed manually against the receiving portion.

The dimensions of the end portion 22, the head 15 and the receiving portion 1 are selected such that the force which is required overcome the frictional force of the self-locking connection between the end portion 22 and the head 15 is tolerable during surgery.

Figure 5A:
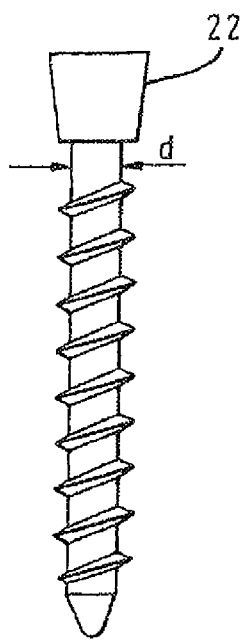
FIGS. 5*a* to 5*c* show modifications of the shank of the anchoring element.
Figure 5B:
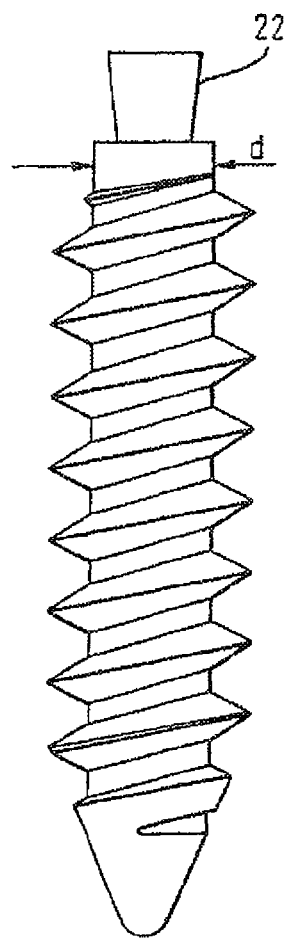
Figure 5C:
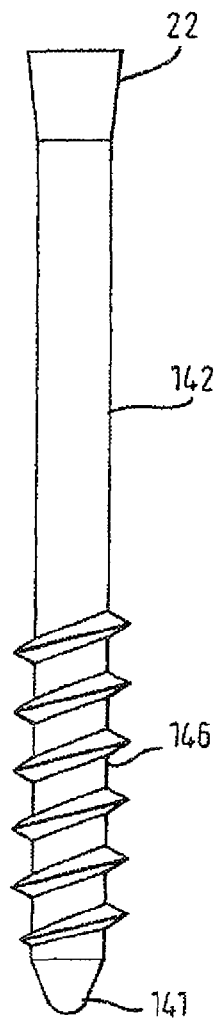

FIGS. 5a to 5c show modifications of the shank 14. In FIG. 5a the diameter d of the shank 14 is smaller than the smallest diameter of the conical portion 22. In FIG. 5b the diameter d of the shank 14 is larger than the smallest diameter of the conical end portion 22. In FIG. 5c the shank comprises a threaded section 140 adjacent to the tip 141 and a section 142 without a bone thread. In all modifications the conical end portion 22 is shaped so as to be receivable in the recess 25 of the head 15.

FIG. 6 shows a schematic view of a modification of the head. The head 15' has the recess 25 shaped as a truncated cone as in the embodiment shown in FIGS. 1 to 4. However the coaxial bore 24' has a diameter which is smaller than the diameter of the end 23 of the conical end portion of the shank. Thus, the upper wall of the recess 25 forms a ring-shaped abutment 28 for the end portion 22. The diameter of the bore 24' is sufficiently large to provide access to the end portion 22 for a screwing-in tool. To allow for an in situ separation of the head 15' together with the receiving portion 1 from the shank 14, the head has engagement means for engagement with a tool which holds the head so that it cannot be drawn against the opening 6 when the receiving portion 1 is pulled away from the shank. FIG. 7 shows an example of a tool 30 which consists of a handle 31 and a bar 32 extending from the handle and having a threaded end portion 33, sometimes called a threaded tip. In this case the bore 24' comprises an inner thread for engagement with the threaded end portion 33. In use, after removal of the inner screw 21 and the rod 20 (see FIG. 1), and thus relieving the pressure on the head 15', the head is held with the tool 30 by screwing in the threaded end portion 33 into the threaded bore 24' and simultaneously the receiving portion is manually pulled away from the shank. According to this manner, the end portion 22 of the shank is drawn out of the head 15.

The invention is not limited to the embodiments described above. Further modifications are conceivable. For example, the invention is not limited to an anchoring element having a threaded shank, but can also be applied to an anchoring element consisting of a hook. In this case, the free end of the hook has the conical end portion 22.

Furthermore, the shape and diameter of the shank 14 can be varied and the length of the bone thread can be varied, too. For example, the modification of FIG. 5c where a shank has a thread-free section can also be applied to the shank shown in FIG. 5a or 5b.

The cone angle of the conical end portion 22 and the recess 25 of the shape of a hollow truncated cone can be selected such that there is no self-locking effect. In this case, the number and the shape of the slits 27 in the head 15 have to be selected such that it is possible to snap the head 15 onto the conical end portion 22.

Instead of several slits in the head 15, it is possible to have only one continuing slit, which extends in a longitudinal direction through the whole wall from one end to the other end of the head. It is also possible to have the continuing slit in addition to the slits shown in FIG. 3. Additional slits may be provided which are open towards the end opposite to the lower opening 26. Further, it is also possible that the recess 25 shaped as a hollow truncated cone extends through a whole head 15, thus, omitting the bore 24 or 24'.

In a further modification, the head is formed of a material providing elasticity, for example, of a suitable plastic material. In this case, the slits may be omitted.

The receiving portion can be modified, too. The radius of the spherical portion 7 can be larger than the radius of the head, as long as the opening 6 is small enough that the head 15 cannot fall out. Instead of the spherical section 7 a section with another shape, for example a conical shape is possible.

Furthermore, the pressure element 17 may have a different shape. The length of the pressure element in a longitudinal direction can be as large that the legs being generated by the U-shaped recess 19 project above the rod when the rod is inserted. In this case it is possible to separately fix the head 15 via the pressure element with an inner nut to be screwed in between the legs 9, 10 and separately fix the rod by an inner screw to be screwed into the nut.

The receiving portion can be part of a bone plate. In this case, the receiving portion does not have a U-shaped recess and pressure onto the head 15 can be generated by, for example, an inner screw solely.

Various other modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A bone anchoring device comprising:
   an anchoring element comprising a shank having a free end and a bone engagement end opposite the free end, the bone engagement end having a bone engagement structure to be anchored to a bone or a vertebra, the anchoring element further comprising a head, the head having an exterior surface with a spherical segment-shaped portion, wherein said shank and said head are separate parts;
   a receiving portion comprising a first end, a second end opposite to the first end, a longitudinal axis passing through the two ends, a bore coaxial with the longitudinal axis, and a first region adjacent to the second end for receiving the spherical segment-shaped section of said head, the receiving portion further comprising a U-shaped recess extending from the first end in the direction of the second end which forms a channel to receive a rod;
   a rod to exert pressure on said head to lock said head in the receiving portion when the rod is received in the channel of the receiving part; and
   a locking element configured to be located in the U-shaped recess to lock the rod;
   wherein said head has a hollow inner portion to receive a free end portion of said shank, wherein said free end portion increases in diameter towards the free end of the shank opposite the bone engagement end of the shank;
   wherein the greatest diameter of the free end portion of the shank is greater than an opening to the hollow inner portion of the head;
   wherein the head has a slit extending from the opening to the hollow inner portion of the head such that, upon engagement and movement of the head and shank toward each other while the head is located in the receiving part, the opening elastically widens to allow insertion of the greatest diameter of the free end portion of the shank through the opening into the hollow inner portion and then narrows to hold the free end portion after insertion.

2. The bone anchoring device of claim 1, wherein the hollow inner portion of the head has a mating shape corresponding to the free end portion of the shank.

3. The bone anchoring device according to claim 1, wherein the head comprises a spring-like edge at the opening to the hollow inner portion of the head.

4. The bone anchoring device of claim 1, wherein the head comprises a plurality of slits extending from the opening and which are directed substantially parallel to the rotational axis of the head.

5. The bone anchoring device of claim 1, wherein the hollow inner portion of the head which receives the free end portion of the shank forms an abutment for the free end of the free end portion.

* * * * *